United States Patent [19]

VandenBerg

[11] Patent Number: Plant 7,464

[45] Date of Patent: Mar. 5, 1991

[54] CHRYSANTHEMUM PLANT NAMED PALOMA

[75] Inventor: Cornelis P. VandenBerg, Salinas, Calif.

[73] Assignee: Yoder Brothers, Inc., Barberton, Ohio

[21] Appl. No.: 408,363

[22] Filed: Sep. 18, 1989

[51] Int. Cl.[5] ..... A01H 5/00

[52] U.S. Cl. ..... Plt./77

[58] Field of Search ..... Plt./76, 77

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Paloma particularly characterized by its flat capitulum form; decorative capitulum type; clear white ray floret color; diameter across face of capitulum of up to 9 cm at maturity; uniform eight week photoperiodic flowering response to short days; peduncle length ranging from 10 to 20 cm on open, terminal sprays; medium plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora*, and referred to by the cultivar name Paloma.

Paloma, identified as 85-263002, was originated from a cross made by Cornelis P. VandenBerg in a controlled breeding program in Salinas, Calif., in 1984.

The female parent of Paloma was an unnamed seedling identified as 81-614001, a cut spray mum with white ray floret color, decorative capitulum type, nine week photoperiodic flowering response to short days, and medium height. The male parent of Paloma was an unnamed seedling, identified as 82-J38047, a cut spray mum having white ray floret color, decorative duplex capitulum type, eight week photoperiodic flowering response to short days, and medium plant height.

Paloma was discovered and selected as one flowering plant within the progeny of the stated cross by Cornelis P. VandenBerg in March, 1986, in a controlled environment in Salinas, Calif.

The first act of asexual reproduction of Paloma was accomplished when vegetative cuttings were taken from the initial selection in May, 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Paloma are firmly fixed and are retained through successive generations of asexual reproduction.

Paloma has not been observed under all possible environmental conditions. The phenotype may vary significantly with variations in environment such as temperature, light intensity and daylength.

The following observations, measurements and comparisons describe plants grown in Salinas, Calif., under greenhouse conditions which approximate those generally used in commercial greenhouse practice. The low temperature tolerance was determined in repeated flowerings in Bogota, Colombia.

The following traits have been repeatedly observed and are determined to be basic characteristics of Paloma, which, in combination, distinguish this Chrysanthemum as a new and distinct cultivar:

1. Flat capitulum form.
2. Decorative capitulum type.
3. White ray floret color.
4. Diameter across face of capitulum up to 9 cm at maturity.
5. Uniform eight week photoperiodic flowering response to short days.
6. Peduncle length ranging from 10 to 20 cm on open terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Paloma, with the colors being as nearly true as possible with illustrations of this type. Sheet 1 is a color photograph of Paloma grown as a single stem cut spray mum. Sheet 2 is a black and white photograph of three views of the inflorescence of Paloma. Sheet 3 is a black and white photograph showing the upper and under sides of the leaves of Paloma at three stages of development (mature, intermediate and immature).

Of the commercial cultivars known to the inventor, the most similar in comparison to Paloma is the unpatented cultivar identified as Polaris. Reference is made to attached Chart A, which compares certain characteristics of Paloma to the same characteristics of Polaris.

Similar traits are capitulum form and type, spray formation, peduncle length, plant height and low temperature tolerance. Paloma has a clear white flower color compared to a creamy white flower color of Polaris. Paloma also has a slightly larger flower, and a faster flowering response by three to four days than Polaris.

In the following description color references are made to the Royal Horticultural Society Color Chart. The clear white ray floret color of Paloma is not represented in the RHS color chart. The color values were determined on plant material grown in Salinas, Calif. on Apr. 26, 1989.

Classification:

*Botanical.*—*Dendranthema grandiflora* cv Paloma.

*Commercial.*—Decorative cut spray mum.

INFLORESCENCE

A. Capitulum:

*Form.*—Flat.

*Type.*—Decorative.

*Diameter across face.*—Up to 9 cm at maturity.

B. Corolla of ray florets:

*Color (general tonality from a distance of three meters).*—Clear white.

*Color (upper surface).*—Clear white.

*Color (under surface).*—Clear white.

*Shape.*—Straight, cross-section flat, apex concave.

C. Corolla of disc florets:

*Color (mature).*—Closest to 14A.

*Color (immature).*—Closest to 145B.

D. Reproductive organs:

*Androecium.*—Present on disc florets only; very few disc florets, barely visible in the mature flower; scant pollen.

*Gynoecium.*—Present on both ray and disc florets.

PLANT

A. General appearance:

*Height.*—Medium; 90 to 100 cm as a single stem cut mum with two long day weeks prior to short days.

B. Foliage:

*Color (upper surface).*—147A.

*Color (under surface).*—147B.

*Shape.*—Lobed, slightly serrated.

CHART A

COMPARISON OF PALOMA AND POLARIS

| | PALOMA | POLARIS |
|---|---|---|
| Ray Floret Color | Clear white | Creamy white |
| Capitulum Form and Type | Flat decorative | Flat decorative |
| Spray formation | Terminal | Terminal |
| Peduncle length | 10 to 20 cm | 10 to 20 cm |
| Diameter Across Face of Capitulum | Up to 9 cm | Up to 8 cm |
| Plant Height | Medium | Medium |
| Flowering response period | 8 weeks | 9 weeks |
| Low temperature tolerance | Excellent | Excellent |

Comparisons Made of Plants Grown As Single Stem Spray Cut Mums In Salinas, California

I claim:

1. A new and distinct Chrysanthemum plant named Paloma, as described and illustrated.

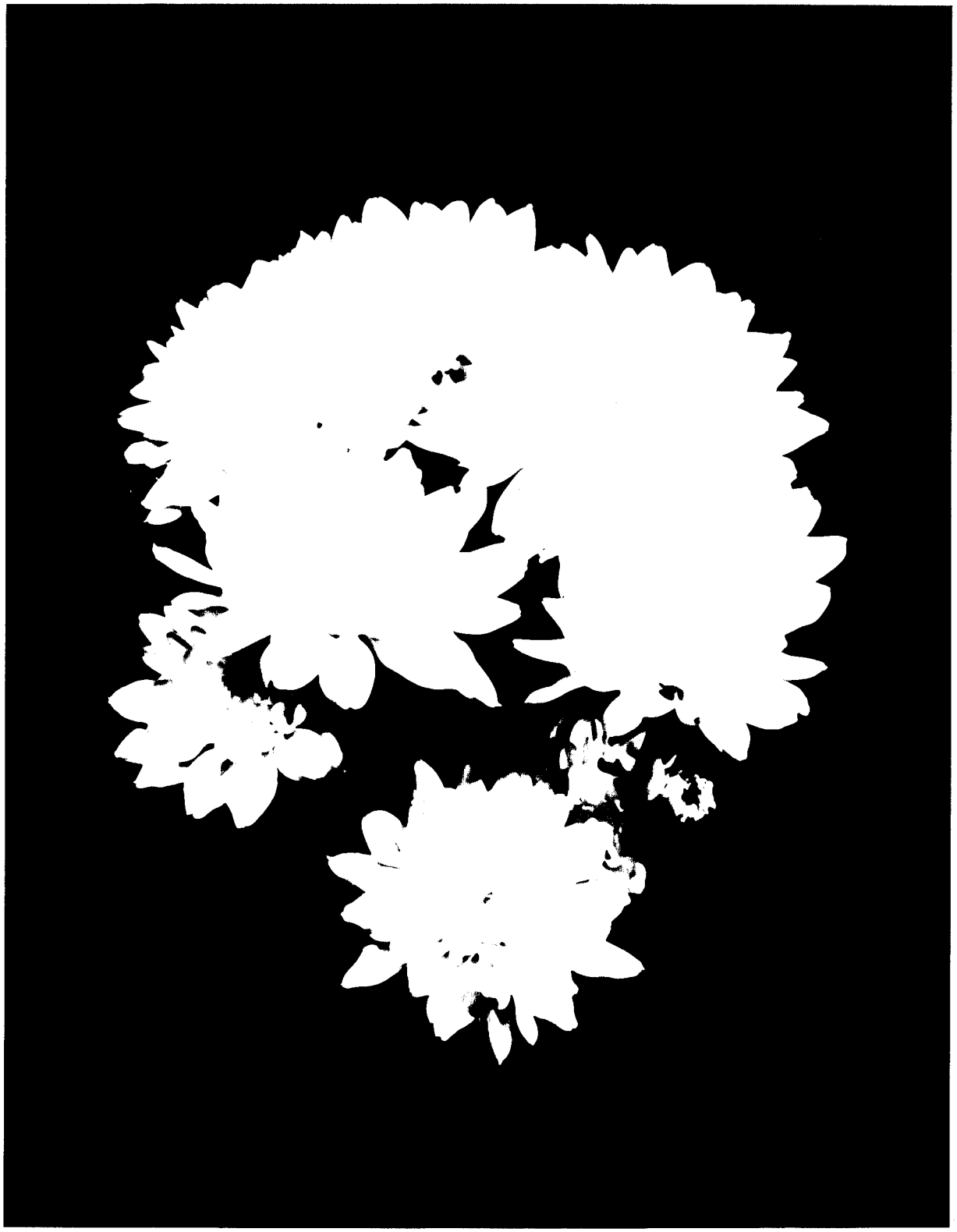

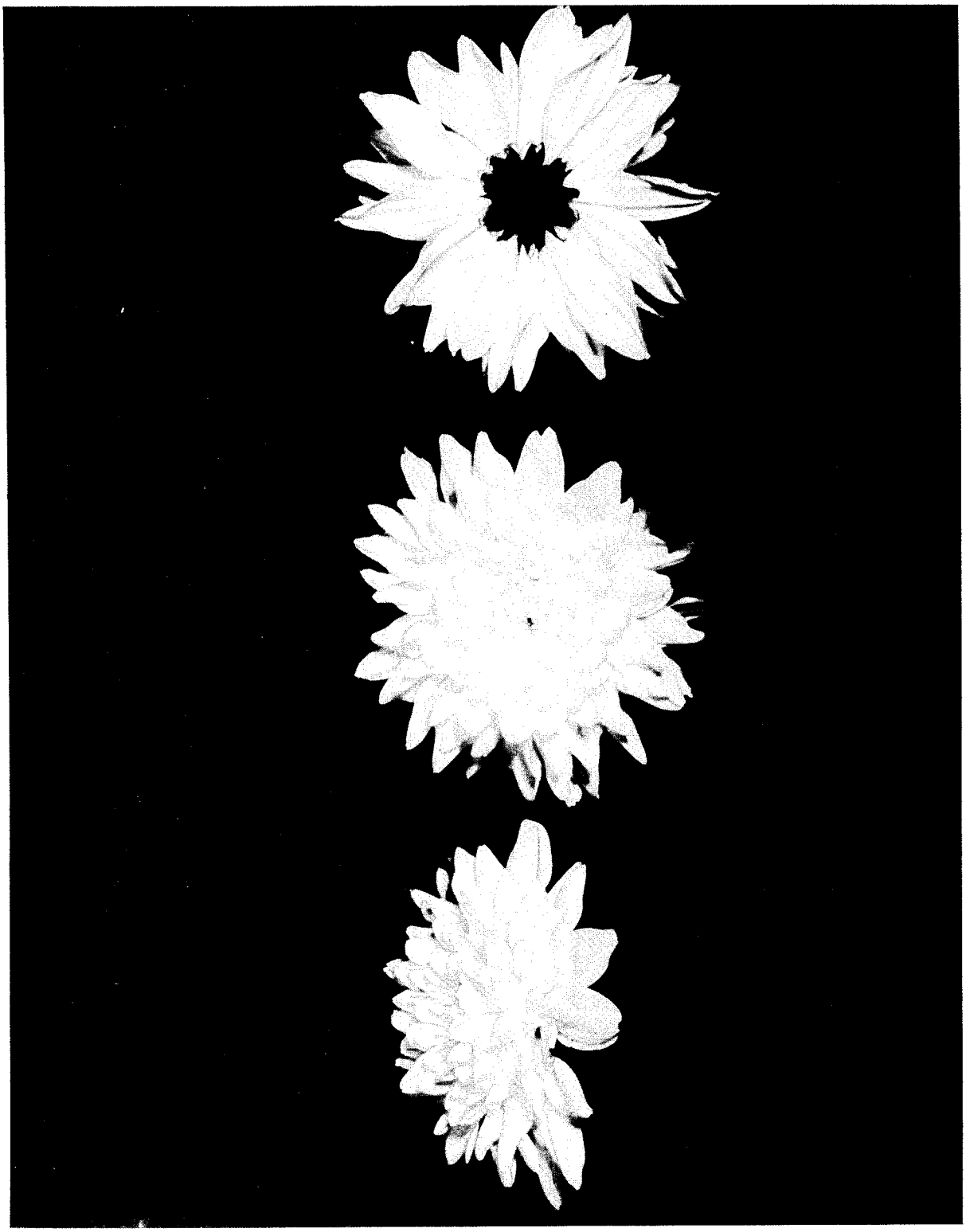

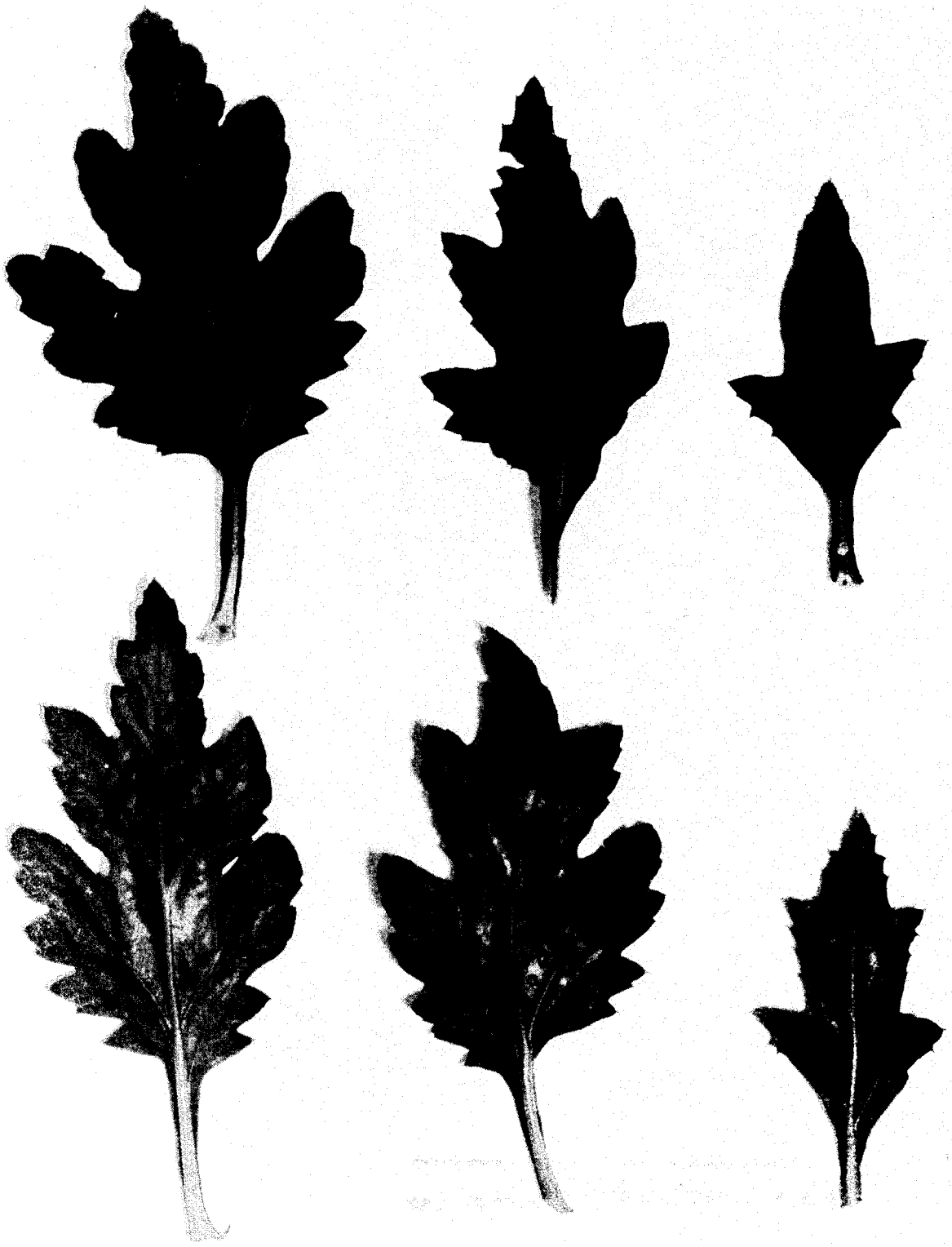

* * * * *